(12) United States Patent
Ishii et al.

(10) Patent No.: US 6,689,920 B2
(45) Date of Patent: Feb. 10, 2004

(54) BIFUNCTIONAL BIPHENYL AND PROCESS FOR PRODUCING BIFUNCTIONAL PHENYLENE ETHER OLIGOMER COMPOUND USING THE SAME

(75) Inventors: Kenji Ishii, Tokyo (JP); Kiyonari Hiramatsu, Tokyo (JP); Makoto Miyamoto, Tokyo (JP); Yasumasa Norisue, Tokyo (JP); Katsuhiko Yanagida, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 10/270,678

(22) Filed: Oct. 16, 2002

(65) Prior Publication Data
US 2003/0229256 A1 Dec. 11, 2003

(51) Int. Cl.⁷ ................................................ C07C 41/00
(52) U.S. Cl. ........................ 568/638; 528/212; 528/219; 568/636; 568/637; 568/730
(58) Field of Search ................................ 568/638, 636, 568/637; 528/212, 219

(56) References Cited

U.S. PATENT DOCUMENTS

| 3,287,421 A | * | 11/1966 | Fox |
| 5,194,563 A | * | 3/1993 | Hay |
| 6,576,800 B2 | * | 6/2003 | Higashimura |
| 2003/0130438 A1 | * | 7/2003 | Amagai |

* cited by examiner

Primary Examiner—Michael L. Shippen
(74) Attorney, Agent, or Firm—Wenderoth, Lind & Ponack, LLP (57) ABSTRACT

A process for producing 2,2',3,3',5,5'-hexamethyl-[1,1'-biphenyl]-4,4'-diol, which process comprises, while setting a pH of a reaction liquid containing an alkaline aqueous solution, a surfactant, a copper catalyst and 2,3,6-trimethylphenol during a reaction in the range of from 8 to 14 and controlling the variation range of the pH of the reaction liquid within ±1, oxidatively coupling the 2,3,6-trimethylphenol with an oxygen-containing gas, and a process for producing a bifunctional phenylene ether oligomer compound having a controlled average molecular weight, comprising carrying out oxidation polymerization under a proper oxygen concentration.

6 Claims, 1 Drawing Sheet

Fig.1

BIFUNCTIONAL BIPHENYL AND PROCESS FOR PRODUCING BIFUNCTIONAL PHENYLENE ETHER OLIGOMER COMPOUND USING THE SAME

FIELD OF THE INVENTION

The present invention relates to a process for producing 2,2',3,3',5,5'-hexamethyl-(1,1'-biphenyl)-4,4'-diol (to be sometimes referred to as "HMBP" hereinafter) and a process for producing abifunctional phenylene ether oligomer having a phenolic hydroxyl group at each terminal by using HMBP. More specifically, it relates to a process for producing HMBP useful for applications such as an intermediate for electronic material and an agricultural chemical intermediate and to a process for selectively producing a bifunctional phenylene ether oligomer which is excellent in electric characteristics, toughness, compatibility with a thermosetting resin and molding-processability and has a predetermined number average molecular weight.

BACKGROUND OF THE INVENTION

As a method for synthesizing a biphenol compound by oxidatively coupling a phenol compound with an oxygen-containing gas, there is a method in which a substance selected from the group consisting of hydroxides, carbonates and bicarbonates of alkali metals, as a basic substance, is used in an aqueous solution containing an anion surfactant in the presence of a copper catalyst (JP-A-51-43748). When the above method is applied to 2,6-dimethyl phenol represented by the formula (3), 3,3',5,5'-tetramethyl-[1,1'-biphenyl]-4,4'-diol (to be referred to as "TMBP" hereinafter) represented by the formula (4) can be obtained relatively at high yield. However, since the aqueous solvent containing the surfactant is strongly stirred (6,000–10,000 rpm), a problem is that intense foaming occurs. Further, the above method requires a special device.

(3)

(4)

Further, there is known a method which does not require a high-speed rotation thanks to an addition of a boron compound as a pH controlling agent (JP-A-60-152433). In particular, this method is effective for an oxidative coupling of an easily oxidizable phenol having substituents at 2- and 6-sites.

Materials for use in an electric or electronic field are required to have low dielectric characteristic for processing high-volume data at high speed in the advanced information society and toughness for preventing the occurrence of microcracks due to thermal shock, etc. For the above requirements, the use of engineering plastic such as polyphenylene ether (to be sometimes referred to as "PPE" hereinafter) is proposed.

PPE has excellent high-frequency properties. On the other hand, known problems of PPE are that it is poor in compatibility with a thermosetting resin such as an epoxy resin or a cyanate resin, that it has a high melt viscosity so that molding-processability is poor, and that a solvent in which it is soluble is limited to an aromatic hydrocarbons solvent such as toluene, benzene or xylene and an halogenated hydrocarbon solvent such as methylene chloride or chloroform so that workability is poor.

For improving the compatibility, a method of improving compatibility by blending PPE with a different resin as a compatibilizing agent is discussed and the pseudo IPN structuralization of PPE and a cyanate resin is also discussed (JP-A-11-21452, etc.). However, problems of molding-processability and heat resistance have not been solved yet. Further, a method of converting a high molecular PPE into a low molecular compound is discussed for improvingmoldability. For example, there are known a method in which a high molecular PPE and a bivalent phenol are redistributed in the presence of a radical catalyst (JP-A-9-291148, etc.) and a method in which a bivalent phenol and a monovalent phenol are subjected to oxidation polymerization (JP-B-8-011747). However, a polymer is present in each of the above methods so that it is impossible to efficiently obtain a bifunctional phenylene ether oligomer compound having a desired molecular weight.

SUMMARY OF THE INVENTION

It is an object of the present invention 1 to provide a process for producing biphenol (to be sometimes referred to as "HMBP" hereinafter) of the formula (2) at high yield without the generation of byproducts by oxidation coupling of alkyl phenol while inhibiting the generation of diphenoquinone.

It is an object of the present invention 2 to provide a process for selectively producing a bifunctional phenylene ether oligomer compound having a PPE structure and a desired number average molecular weight which oligomer compound has the excellent electric characteristics and toughness of PPE and is improved in compatibility with a thermosetting resin and molding-processability.

It is another object of the present invention to provide a process for selectively producing a bifunctional phenylene ether oligomer compound having a PPE structure and a desired number average molecular weight which oligomer compound is soluble in a general-purpose ketone solvent and has terminal phenolic hydroxyl groups which are easily modifiable.

According to the present invention 1, there is provided a process for producing HMBP of the formula (2), which process comprises, while setting a pH of a reaction solution containing an alkaline aqueous solution, a surfactant, a copper catalyst and 2,3,6-trimethylphenol represented by the formula (1) during a reaction in the range of from 8 to 14 and controlling the variation range of the pH of the reaction solution within ±1, oxidatively coupling the 2,3,6-trimethylphenol with an oxygen-containing gas.

(1)

(2)

According to the present invention 2, there is provided a process for producing a bifunctional phenylene ether oligomer compound having a controlled average molecular weight, represented by the formula (5), comprising carrying out oxidation polymerization at an oxygen concentration lower than an oxygen concentration of an explosion limit of a solvent to be used by charging a reactor with a mixture containing a catalyst, an amine and a solvent in advance and then dropwise adding a mixture containing HMBP of the following formula (2), a monovalent phenol of the following formula (6), an amine and a solvent to the mixture in the reactor, thereby producing a bifunctional phenylene ether oligomer of the formula (5), wherein, from a moment when the number average molecular weight of the bifunctional phenylene ether oligomer compound exceeds 500, the supply rate of the dropwise addition mixture is controlled such that the concentration of the monovalent phenol of the formula (6) in the reactor does not exceed 15% by weight based on the total amount of the above monovalent phenol, the bifunctional phenylene ether oligomer and the HMBP [(6)/(5)+(2)+(6)<0.15], (5)

(2)

(6)

in which $R^1$ and $R^2$ may be the same or different and are a halogen atom, an alkyl group having 6 or less carbon atoms or a phenyl group, $R^3$ and $R^4$ may be the same or different and are a hydrogen atom, a halogen atom, an alkyl group having 6 or less carbon atoms or a phenyl group, and each of m and n is an integer of 0 to 25 while at least one of m and n is not 0.

According to the present invention 2, further, there is provided a process according to the above, wherein the mixture containing the catalyst, the amine and the solvent charged in the reactor in advance further contains HMBP.

According to the present invention 2, further, there is provided A process according to the above, wherein the molar ratio between the HMBP of the formula (2) and the monovalent phenol of the formula (6) is 1:1 to 1:15.

DETAILED DESCRIPTION OF THE INVENTION

The present inventors have made diligent studies on a process for producing biphenol by oxidative coupling of alkyl phenol and as a result found that, by carrying out oxidative coupling of 2,3,6-trimethylphenol (to be sometimes referred to as "TMP" hereinafter) of the formula (1) in an alkaline aqueous solution having a high pH range while precisely retaining the pH in a specified range, HMBP of the formula (2) can be produced more efficiently than other methods without generating diphenoquinone. On the basis of the above finding, the present inventors have completed the present invention 1. Even a very small quantity of diphenoquinone causes coloring and is difficult to remove so that it is important that diphenoquinone is not generated. The present invention 1 will be explained in detail hereinafter.

A general oxidation coupling reaction has a tendency in which pH decreases as the reaction proceeds. That is, for carrying out synthesis efficiently, it is required to maintain the pH in the alkali range at all times. Further, it is required to control the pH at a high degree for obtaining biphenol stably. However, when 2,6-dimethylphenol represented by the formula (3) is used as a raw material, it is found that the generation of polyphenylene ether is promoted or that the generation of a diphenoquinone compound is promoted since TMBP itself of the formula (4), which is a product and is bivalent phenol, is apt to be easily oxidized. Therefore, it is impossible to obtain a desired biphenol efficiently.

However, when monovalent phenol of the formula (1) is used, its oxidation is prevented by the influence of a methyl group at 3-site in its structure and therefore the generation of diphenoquinone is suppressed. Further, the present inventors have found that HMBP of the formula (2) can be synthesized at high yield by maintaining the pH of a reaction solution in the range of 8 to 14, more preferably in the range of 11.5 to 13.5, and controlling the pH during a reaction within ±1, preferably ±0.5.

The monovalent phenol of the present invention is 2,3,6-trimethylphenol (TMP) represented by the formula (1) and is indispensably required to have a methyl group at 3-site, counted from the phenolic hydroxyl group.

(1)

The bivalent phenol synthesized by the present invention 1 is 2,2',3,3',5,5'-hexamethyl-[1,1'-biphenyl]-4,4'-diol (HMBP) as shown in the following formula (2).

(2)

As a base for adjusting the pH of the reaction solution, it is preferred to use one kind of base or at least two kinds of bases selected from sodium hydroxide, potassium hydroxide, sodium hydrogencarbonate, disodium hydrogenphosphate and potassium dihydrogen phosphate. By using the above base(s), the pH of the aqueous solution can be controlled in the pH range of 8 to 14. By controlling the pH during the reaction within ±1, preferably ±0.5, within the pH range of 8 to 14, preferably within the pH range of 10 to 14, more preferably within the pH range of 11.5 to 13.5, the HMBP can be produced at high yield without generating diphenoquinone.

As a pH controlling agent, sodium hydroxide or potassium hydroxide is particularly preferably used. As a basic hydroxide, there may be used hydroxides of barium, calcium, magnesium and the like other than the above hydroxides.

The molar ratio of the base to be used to the phenol as a raw material is preferably 3 to 25 mol %.

The surfactant suitable for use includes, for example, fatty acid soap, alkylsulfonate salt, alkyl benzene and alkyl naphthalene sulfonate salts, alkyl sulphate salt and alkyl ether phosphate salt.

As a catalyst used when the oxidative coupling reaction is carried out by using an oxygen-containing gas, there is used one kind of metal salt or at least two kinds of metal salts such as cupric acetate, cupric chloride, cupric bromide, cupric iodide, copper carbonate, copper nitrate and copper sulfate. The catalyst shall not be specially limited to these, so long as it is a metal salt.

Problems such as clogging of a condenser can be prevented by applying pressure to a reactor. The pressure to be applied to the reactor is preferably 0.3 to 10.0 kg/cm$^2$G. Further, it is more preferred to invariably maintain a constant pressure during the reaction by attaching a pressure regulating valve.

Although the reaction temperature in the production process of the present invention 1 is not specially limited, it is preferably 70 to 98° C. When it is lower than 70° C., it is lower than the melting point of TMP so that reaction efficiency is poor. Further, since the inflammation point of TMP is 98.8° C., a reaction temperature lower than 98.8° C. is preferred in view of safety. More preferably, it is 75 to 90° C.

As a stirrer to be used, there may be used a general stirrer. Stirring is carried out at 300 to 1,200 rpm. When the speed of the stirring is lower than 300 rpm, oxygen is insufficiently taken in, so that oxidizing velocity decreases. On the other hand, when it is higher than 1,200 rpm, it becomes a significant industrial interference.

Then, the process for producing a bifunctional phenylene ether oligomer compound, provided by the present invention 2, will be explained.

The present inventors have made diligent studies on a process for producing a bifunctional phenylene ether oligomer and as a result found the following. A reactor is charged with a mixture containing a catalyst, an amine and a solvent, and optionally HMBP of the formula (2), in advance. A mixture containing HMBP of the formula (2), a monovalent phenol of the formula (6), an amine and a solvent is dropwise added to the reactor. From a moment when the number average molecular weight of a bifunctional phenylene ether oligomer compound of the formula (5) exceeds 500, oxidation polymerization is carried out by controlling the supply rate of the above dropwise addition mixture such that the concentration of the monovalent phenol of the formula (6) in the reactor does not exceed 15% by weight based on the total amount of the above monovalent phenol, the bifunctional phenylene ether oligomer and the HMBP [(6)/(5)+(2)+(6)<0.15], whereby a bifunctional phenylene ether oligomer having a desired number average molecular weight, represented by the formula (5), can be stably and efficiently obtained. On the basis of the above finding, the present inventors have completed the present invention.

(5)

(2)

(6)

wherein R$^1$ and R$^2$ may be the same or different and are a halogen atom, an alkyl group having 6 or less carbon atoms or a phenyl group, $R^3$ and $R^4$ may be the same or different and are a hydrogen atom, a halogen atom, an alkyl group having 6 or less carbon atoms or a phenyl group, and each of m and n is an integer of 0 to 25 while at least one of m and n is not 0.

The HMBP of the formula (2) in the present invention can be obtained by oxidatively coupling 2,3,6-trimethylphenol (sometimes called TMP) represented by the formula (1), as shown in, for example, Japanese Patent Application No. 2001-319064.

The monovalent phenol in the present invention 2 is a monovalent phenol which is represented by the formula (6). It is preferred that a monovalent phenol having substituents at the 2- and 6-sites of the formula (6) is used alone or used in combination with a monovalent phenol having substituents at the 2-, 3- and 6-sites or at the 2-, 3-, 5- and 6-sites of the formula (6). More preferably, when used alone, 2,6,-dimethyl phenol is preferred, and when used in combination, 2,6,-dimethyl phenol and 2,3,6-trimethyl phenol are preferred.

The bifunctional phenylene ether oligomer represented by the formula (5) in the present invention 2 is obtained by carrying out oxidation polymerization of the HMBP of the formula (2) and the monovalent phenol of the formula (6). As an oxidation method, there is a method in which an oxygen gas or air is directly used. There is also an electrode-oxidation method. Any methods may be used, and the oxidation method is not specially limited. In view of low-cost investment in plant and equipment, air oxidation is preferred. In view of safety, it is more preferred to carry out the oxidation polymerization at an oxygen concentration in a reactor which is lower than a limit oxygen concentration of the explosion limit. As an oxidation polymerization method at an oxygen concentration lower than the limit oxygen concentration, there is selected a method in which oxidation polymerization is carried out with air while supplying an inert gas into a gaseous phase or a method in which oxidation polymerization is carried out with a mixed gas having an oxygen concentration of 3 to 15% which is obtained by mixing air with an inert gas, etc. For carrying out the oxidation polymerization, there is generally adopted a pressure of from atmospheric pressure to 20 kg/cm$^2$.

As a catalyst used for the oxidation polymerization, there is used a copper salt such as CuCl, CuBr, Cu$_2$SO$_4$, CuCl$_2$, CuBr$_2$, CuSO$_4$ and CuI. These copper salts may be used alone or in combination. The catalyst is not specially limited to these. These catalysts may be used in combination with one amine or two or more amines. The amine includes mono- and dimethylamines, mono- and diethylamines, mono-and dipropyl amines, mono- and di-n-butylamines, mono- and di-sec-dipropylamines, mono- and dibenzylamines, mono-and dicyclohexylamines, mono- and diethanolamines, ethylmethylamine, methylpropylamine, butyldimethylamine, allylethylamine, methylcyclohexylamine, morpholine, methyl-n-butylamine, ethylisopropylamine, benzyl methyl amine, octylbenzylamine, octyl-chlorobenzylamine, methyl (phenylethyl)amine, benzylethylamine, N-n-butyldimethylamine, N,N'-di-tert-butylethylenediamine, di(chlorophenylethyl)amine, 1-methylamino-4-pentene, pyridine, methylpyridine, 4-dimethylaminopyridine and piperidine. The catalysts shall not be limited to these examples, and any other copper salts and amines may be used.

When the oxidation polymerization in the present invention 2 is carried out by a batch method, the polymerization is carried out as follows. A mixture containing the catalyst, the amine and the solvent is placed in a reactor in advance and a mixture containing the HMBP of the formula (2), the monovalent phenol of the formula (6) and the amine and the solvent is dropwise added to the reactor. From a moment when the number average molecular weight of bifunctional phenylene ether oligomer compound of the formula (5) exceeds 500, oxidation polymerization is carried out while controlling the supply rate of the above dropwise addition mixture such that the concentration of the monovalent phenol of the formula (6) in the reactor does not exceed 15% by weight based on the total amount of the above monovalent phenol, the bifunctional phenylene ether oligomer and the HMBP [(6)/(5)+(2)+(6)<0.15]. Further, it is also possible to incorporate part of the HMBP in the reactor in advance for increasing the synthesis efficiency of bifunctional phenylene ether oligomer at the beginning of the reaction. The present reaction may be carried out using a continuous reaction equipment as required. With regard to the amine, the following is preferred. 20 to 70% by weight, based on a required amount, of the amine is placed in the reactor in advance, the residual amine in an amount of 30 to 80% by weight is added to the dropwise addition mixture and the addition mixture is supplied in accordance with the progress of the reaction.

In the present invention 2, the bifunctional phenylene ether oligomer having a desired number average molecular weight, represented by the formula (5), can be efficiently produced by supplying the HMBP of the formula (2) and the monovalent phenol of the formula (6) in a constant molar ratio and allowing these to react. For example, when the molar ratio of HMBP: 2,6-dimethyl phenol as a monovalent phenol is 1:3, a bifunctional phenylene ether oligomer compound having a number average molecular weight of 600 to 700 is obtained. When the above molar ratio is 1:5, a bifunctional phenylene ether oligomer compound having a number average molecular weight of 850 to 950 is obtained. When the above molar ratio is 1:10, a bifunctional phenylene ether oligomer compound having a number average molecular weight of 1,450 to 1,550 is obtained.

In the present invention 2, the supply rate of the raw material phenol is important. From a moment when the number average molecular weight of a generated bifunctional phenylene ether oligomer compound of the formula (5) exceeds 500, it is required to carry out the oxidation polymerization with controlling the supply rate of the above dropwise addition mixture such that the concentration of the monovalent phenol of the formula (6) in the reactor does not exceed 15% by weight based on the total amount of the above monovalent phenol, the bifunctional phenylene ether oligomer compound and the HMBP [(6)/(5)+(2)+(6)<0.15]. The supply rate of the dropwise addition mixture depends on an oxidation polymerization rate of the phenol. Concretely, it depends on oxygen concentration of the oxygen-containing gas to be supplied and a pressure in the reactor. For example, when air oxidation is carried out at normal pressure, regarding the supply rate of the dropwise addition mixture, the dropwise addition mixture is preferably supplied in the range of from 60 minutes to 150 minutes. Further, when oxidation is carried out at normal pressure with a mixed gas having an oxygen concentration of 8%, concerning the supply rate of the phenol solution, the dropwise addition mixture is preferably supplied in the range of from 160 minutes to 360 minutes. When the supply rate is faster than the above ranges, the concentration of the monovalent phenol in the reactor becomes 15% by weight or higher so that there is generated a monofunctional phenylene ether oligomer compound which is a result of oxidation polymerization of only the monovalent phenol and it becomes difficult to obtain a bifunctional phenylene ether oligomer compound having a desired number average molecular weight. When the supply rate of the phenol solution is slower than the above ranges, uneconomically, the reaction time becomes too long.

The present invention 2 is characterized in that the amine to be used is separated in the reactor and in the dropwise addition mixture. 20 to 70% by weight, based on the entire amount of the amine, of the amine is charged in the reactor, and the residual amine in an amount of 30 to 80% is incorporated in the dropwise addition mixture and is supplied in accordance with the progress of the reaction to carry out the oxidation polymerization. When the initial amount of the amine in the reactor exceeds 70% by weight, the reaction explosively proceeds at the beginning of the reaction so that it is difficult to control the molecular weight. When the initial amount of the amine in the reactor is lower than 20% by weight, the catalyst does not works effectively and the reaction at the begging becomes extremely slow so that it is difficult to control the molecular weight.

In the present invention 2, while unreacted phenol remains, the oxidation reaction can be continued after the supply of the raw material phenol is terminated. However, when the oxidation polymerization is continued after all the phenol is reacted, an increase in molecular weight occurs or an undesired side-reaction product generates so that it becomes difficult to efficiently obtain a bifunctional phenylene ether oligomer having a desired molecular weight. Further, since the reaction time becomes longer, it is not economical.

Then, the solvent used in the present invention 2 will be explained. A ketone solvent and an alcohol solvent have been thought to be a poor solvent in oxidation polymerization and the use of these solvents is limited with regard to a conventional oxidation polymerization of PPE, while these solvents maybe used in the present invention 2. Conventionally, this kind of reaction generates a polymer which is hard to solve in an organic solvent. Therefore, it has been impossible to use ketone or alcohol as a reaction solvent. However, the generation product of the present invention 2 is easily dissolved in ketone or alcohol. Accordingly, the range of a usable solvent has broadened greatly. Each of the ketone solvent and the alcohol solvent may be used alone or in combination with an aromatic hydrocarbon solvent such as toluene, benzene or xylene or a halogenated hydrocarbon solvent such as methylene chloride or chloroform, each of which is a conventional solvent. The ketone solvent includes acetone, methyl ethyl ketone, diethyl ketone, methyl butyl ketone and methyl isobutyl ketone. The alcohol solvent includes methanol, ethanol, propanol, isopropanol, butanol, ethylene glycol and propylene glycol. The ketone solvent and the alcohol solvent shall not be limited to these.

The reaction temperature in the production process of the present invention 2 is not specially limited, unless it enters the explosion limit range of a solvent used. It is preferably 30 to 50° C. Since oxidation polymerization is an exothermic reaction, the control of a temperature is difficult and it is hard to control a molecular weight when the reaction temperature is more than 50° C. When the reaction temperature is lower than 30° C., it enters the explosion limit range of some solvents, so that safety production can not be carried out.

The present invention will be explained more in detail with reference to Examples hereinafter. In Examples, "%" stands for "% by weight" unless otherwise specified.

A manufacturing equipment, shown in FIG. 1, suitable for use in the present invention 1 will be explained. The equipment of FIG. 1 comprises a stainless-steel reactor 8 equipped with a stirrer 1 with a stirring blade 9, an oxygen-introducing tube 2 (with a pressure gauge 3 and a pressure regulating valve 4) from an oxygen supply source such as an oxygen bomb 10, a thermometer (not shown in FIG. 1), an alkali injection vessel 6 (1 N alkali hydroxide aqueous solution is used) with a pH controller 5 and baffleplates 7. The working method of the present equipment is as follows. The reactor 8 is charged with TMP and a pH controlling agent, a copper catalyst is added at the moment when the temperature becomes 60° C., then the pressure regulating valve and the pH controller are actuated, further the temperature is increased up to 85° C. and stirring is carried out at 500 rpm. The total length of the stirring blade is ⅓ of the diameter of the reactor. As a baffleplate, four baffleplates are attached. The reactor-diametral-direction length of each baffleplate is 1/10 of the diameter of the reactor.

EXAMPLES

Example 1

A stainless-steel reactor having a volume of 40 liters was charged with 4,000 g (29.4 mol) of 2,3,6-trimethylphenol (TMP), 21 g of sodium hydroxide (pH controlling agent), 18 g of sodium lauryl sulfate (surfactant) and 18,000 g of pure water, the mixture was heated up to 60° C., and at the time when the temperature reached 60° C., 0.6 g (0.003 mol) of cupric acetate was added. At this point of time, the pH was 12.8. A pressure control was actuated to adjust the inner pressure at 0.5 kg/cm$^2$G, and stirring was carried out at 500 rpm. The mixture was further heated up to 85° C. The pH was controlled at 13±0.5 using a pH controller shown in FIG. 1. At the time when oxygen absorption disappeared, the heating was terminated to finish the reaction. At this point of time, the pH was 13.1. Then, 1 N hydrochloric acid aqueous solution was added to decrease the pH to 4. Then, filtration was carried out to obtain a solid, the solid was washed with pure water and then washed with hot water and toluene. Drying under reduced pressure was carried out at 80° C. to obtain 3,529 g (yield 89%) of a white powder. Diphenoquinone was not found in the white powder (detection limit 0.01%).

Example 2

A stainless-steel reactor having a volume of 40 liters was charged with 4,000 g (29.4 mol) of 2,3,6-trimethylphenol (TMP), 1,456 mL of 0.1N sodium hydroxide and 125 g of disodium hydrogenphosphate as pH controlling agents, 18 g of sodium lauryl sulfate (surfactant) and 16,500 g of pure water, the mixture was heated up to 60° C., and at the time when the temperature reached 60° C., 0.6 g (0.003 mol) of cupric acetate was added. At this point of time, the pH was 11.2. A pressure control was actuated to adjust the inner pressure at 0.5 kg/cm$^2$G, and stirring was carried out at 500 rpm. The mixture was further heated up to 85° C. The pH was controlled at 11±0.5 using a pH controller shown in FIG. 1. At the time when oxygen absorption disappeared, the heating was terminated to finish the reaction. At this point of time, the pH was 10.8. Then, 1 N hydrochloric acid aqueous solution was added to decrease the pH to 4. Then, filtration was carried out to obtain a solid, the solid was washed with pure water and then washed with hot water and with toluene.

Drying under reduced pressure was carried out at 80° C. to obtain 3,172 g (yield 80%) of a white powder. Diphenoquinone was not found in the white powder (detection limit 0.01%).

Comparative Example 1

A stainless-steel reactor having a volume of 40 liters was charged with 4,000 g (29.4 mol) of 2,3,6-trimethylphenol (TMP), 21 g of sodium hydroxide (pH controlling agent), 18 g of sodium lauryl sulfate (surfactant) and 18,000 g of pure water, the mixture was heated up to 60° C., and at the time when the temperature reached 60° C., 0.6 g (0.003 mol) of cupric acetate was added. At this point of time, the pH was 12.8. A pressure control was actuated to adjust the inner pressure at 0.5 kg/cm$^2$G, and stirring was carried out at 500 rpm. The mixture was further heated up to 85° C. At the time when oxygen absorption disappeared, the heating was terminated to finish the reaction. At this point of time, the pH was 9.4. Then, 1 N hydrochloric acid aqueous solution was added to decrease the pH to 4. Then, filtration was carried out to obtain a solid, the solid was washed with pure water and then washed with hot water and toluene. Drying under reduced pressure was carried out at 80° C. to obtain 2,736 g (yield 69%) of a yellow powder. It was confirmed that the powder contained 0.2% of diphenoquinone.

Comparative Example 2

A stainless-steel reactor having a volume of 40 liters was charged with 4,000 g (29.4 mol) of 2,3,6-trimethylphenol (TMP), 14 g of potassium dihydrogen phosphate and 189.6 g of disodium hydrogenphosphate as pH controlling agents, 18 g of sodium lauryl sulfate (surfactant) and 18,000 g of pure water, the mixture was heated up to 60° C., and at the time when the temperature reached 60° C., 0.6 g (0.003 mol) of cupric acetate was added. At this point of time, the pH was 8.7. A pressure control was actuated to adjust the inner pressure at 0.5 kg/cm$^2$G, and stirring was carried out at 500 rpm. The mixture was further heated up to 85° C. The pH was gradually increased with a pH controller shown in FIG. 1 such that the pH became 12 at a reaction finish time. At the time when oxygen absorption disappeared, the heating was terminated to finish the reaction. At this point of time, the pH was 12.1. Then, 1 N hydrochloric acid aqueous solution was added to decrease the pH to 4. Then, filtration was carried out to obtain a solid, the solid was washed with pure water and then washed with hot water and toluene. Drying under reduced pressure was carried out at 80° C. to obtain 2,855 g (yield 72%) of a yellow powder. It was confirmed that the powder contained 0.2% of diphenoquinone.

Comparative Example 3

A stainless-steel reactor having a volume of 40 liters was charged with 4,000 g (29.4 mol) of 2,3,6-trimethylphenol (TMP), 23 g of sodium hydroxide (pH controlling agent), 18 g of sodium lauryl sulfate (surfactant) and 18,000 g of pure water, the mixture was heated up to 60° C., and at the time when the temperature reached 60° C., 0.6 g (0.003 mol) of cupric acetate was added. At this point of time, the pH was 12.2. A pressure control was actuated to adjust the inner pressure at 0.5 kg/cm$^2$G, and stirring was carried out at 500 rpm. The mixture was further heated up to 85° C. The pH was controlled with a pH controller, shown in FIG. 1, such that the pH became 9 at a reaction finish time. At the time when oxygen absorption disappeared, the heating was terminated to finish the reaction. At this point of time, the pH was 9.0. Then, 1 N hydrochloric acid aqueous solution was added to decrease the pH to 4. Then, filtration was carried out to obtain a solid, the solid was washed with pure water and then washed with hot water and toluene. Drying under reduced pressure was carried out at 80° C. to obtain 2,895 g (yield 73%) of a yellow powder. It was confirmed that the powder contained 0.2% of diphenoquinone.

Comparative Example 4

A stainless-steel reactor having a volume of 40 liters was charged with 4,000 g (29.4 mol) of 2,3,6-trimethylphenol (TMP), 680 g of sodium hydroxide (pH controlling agent), 18 g of sodium lauryl sulfate (surfactant) and 18,000 g of pure water, the mixture was heated up to 60° C., and at the time when the temperature reached 60° C., 0.6 g (0.003 mol) of cupric acetate was added. At this point of time, the pH was 13.9. A pressure control was actuated to adjust the inner pressure at 0.5 kg/cm$^2$G, and stirring was carried out at 500 rpm. The mixture was further heated up to 85° C. At the time when oxygen absorption disappeared, the heating was terminated to finish the reaction. At this point of time, the pH was 12.1. Then, 1 N hydrochloric acid aqueous solution was added to decrease the pH to 4. Then, filtration was carried out to obtain a solid, the solid was washed with pure water and then washed with hot water and toluene. Drying under reduced pressure was carried out at 80° C. to obtain 2,300 g (yield 65%) of a yellow powder. It was confirmed that the powder contained 0.1% of diphenoquinone.

Comparative Example 5

A stainless-steel reactor having a volume of 40 liters was charged with 4,000 g (29.4 mol) of 2,3,6-trimethylphenol (TMP), 587 g of borax as a pH controlling agent, 18 g of sodium lauryl sulfate (surfactant) and 16,500 g of pure water, the mixture was heated up to 60° C., and at the time when the temperature reached 60° C., 0.6 g (0.003 mol) of cupric acetate was added. At this point of time, the pH was 9.5. A pressure control was actuated to adjust the inner pressure at 0.5 kg/cm$^2$G, and stirring was carried out at 500 rpm. The mixture was further heated up to 85° C. At the time when oxygen absorption disappeared, the heating was terminated to finish the reaction. At this point of time, the pH was 8.8. Then, 1 N hydrochloric acid aqueous solution was added to decrease the pH to 4. Then, filtration was carried out to obtain a solid, the solid was washed with pure water and then washed with hot water and toluene. Drying under reduced pressure was carried out at 80° C. to obtain 2,934 g (yield 74%) of a yellow powder. It was confirmed that the powder contained 0.2% of diphenoquinone.

Comparative Example 6

A stainless-steel reactor having a volume of 40 liters was charged with 3,590 g (29.4 mol) of 2,6-xylenol (2,6-X), 12 g of potassium dihydrogen phosphate and 189.6 g of disodium hydrogenphosphate as pH controlling agents, 18 g of sodiumlauryl sulfate (surfactant) and 18,000 g of pure water, the mixture was heated up to 60° C., and at the time when the temperature reached 60° C., 0.6 g (0.003 mol) of cupric acetate was added. At this point of time, the pH was 8.7. A pressure control was actuated to adjust the inner pressure at 0.5 kg/cm$^2$G, and stirring was carried out at 500 rpm. The mixture was further heated up to 85° C. The pH was controlled at 9±0.5 using a pH controller shown in FIG. 1. At the time when oxygen absorption disappeared, the heating was terminated to finish the reaction. At this point of time, the pH was 9.2. Then, 1 N hydrochloric acid aqueous solution was added to decrease the pH to 4. Then, filtration was carried out to obtain a solid, the solid was washed with pure water and then washed with hot water and toluene. Drying under reduced pressure was carried out at 80° C. to obtain 2,631 g (yield 74%) of a yellow powder. It was confirmed that the powder contained 0.5% of diphenoquinone.

Comparative Example 7

A stainless-steel reactor having a volume of 40 liters was charged with 3,590 g (29.4 mol) of 2,6-xylenol (2,6-X), 21 g of sodium hydroxide (pH controlling agent), 18 g of sodium lauryl sulfate (surfactant) and 18,000 g of pure water, the mixture was heated up to 60° C., and at the time when the temperature reached 60° C., 0.6 g (0.003 mol) of cupric acetate was added. At this point of time, the pH was 12.8. A pressure control was actuated to adjust the inner pressure at 0.5 kg/cm$^2$G, and stirring was carried out at 500 rpm. The mixture was further heated up to 85° C. The pH was controlled at 13±0.5 using a pH controller shown in FIG. 1. At the time when oxygen absorption disappeared, the heating was terminated to finish the reaction. At this point of time, the pH was 13.2. Then, 1 N hydrochloric acid aqueous solution was added to decrease the pH to 4. Then, filtration was carried out to obtain a solid, the solid was washed with pure water and then washed with hot water and toluene. Drying under reduced pressure was carried out at 80° C. to obtain 2,702 g (yield 76%) of a yellow powder. It was confirmed that the powder contained 0.9% of diphenoquinone.

Table 1 shows the above results.

TABLE 1

| | Phenol | Base | pH *1 | pH *2 | Diphenoquinone (%) | Yield (%) | Color of powder |
|---|---|---|---|---|---|---|---|
| Ex.1 | TMP | Sodium hydroxide (pH control) | 12.8 | 13.1 | <0.01 | 89 | White |
| Ex.2 | TMP | Sodium hydroxide and disodium hydrogenphosphate (pH control) | 11.2 | 10.8 | <0.01 | 80 | White |
| CEx.1 | TMP | Sodium hydroxide (no pH control) | 12.8 | 9.4 | 0.2 | 69 | Yellow |
| CEx.2 | TMP | potassium dihydrogen phosphate and disodium hydrogenphosphate (pH control 9→12) | 8.7 | 12.1 | 0.2 | 72 | Yellow |
| CEx.3 | TMP | Sodium hydroxide (pH control 12→9) | 12.2 | 9 | 0.2 | 73 | Yellow |
| CEx.4 | TMP | Sodium hydroxide (no pH control) | 13.9 | 12.1 | 0.1 | 65 | Yellow |
| CEx.5 | TMP | borax (no pH control) | 9.5 | 8.8 | 0.2 | 74 | Yellow |
| CEx.6 | 2,6-X | potassium dihydrogen phosphate and disodium hydrogenphosphate (pH control) | 8.7 | 9.2 | 0.5 | 74 | Yellow |
| CEx.7 | 2,6-X | Sodium hydroxide and disodium hydrogenphosphate (pH control) | 12.8 | 13.2 | 0.9 | 76 | Yellow |

Ex. = Example, CEx. = Comparative Example, *1: pH before the reaction, *2: pH after the reaction The above results clarified the following properties.

(a) When TMP was used as a raw material, the intended compounds were obtained at higher yields as compared with the cases in which 2,6-xylenol was used. Further, when the pH was controlled at ±0.5 in the higher pH region and TMP was used, no generation of diphenoquinone was found. However, when 2,6-xylenol was used, it was confirmed that diphenoquinone was generated.

(b) In the cases in which the variation range of the pH during the reaction was larger than ±1, even when TMP was used, the generation of diphenoquinones was confirmed and the yellow powders were obtained.

Figure 1:
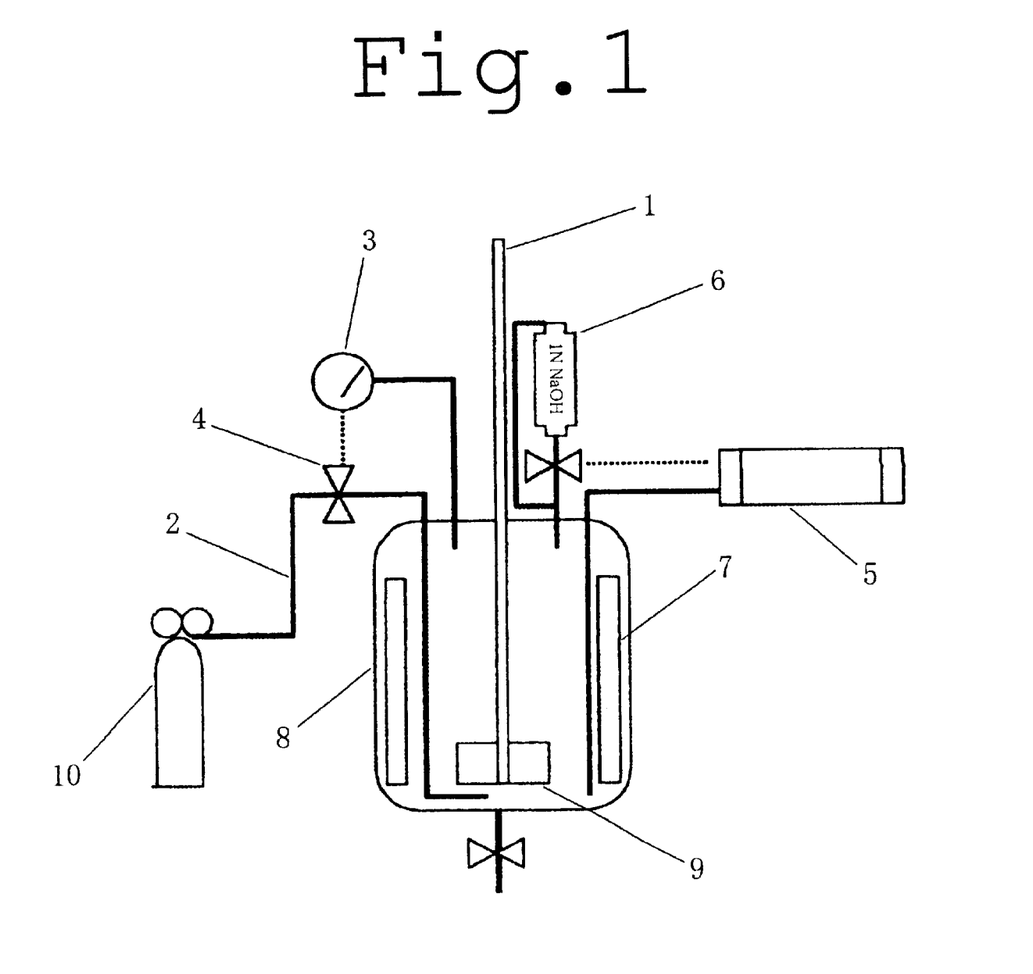
FIG. 1 is an explanatory drawing showing a reaction equipment used in the present invention 1.

(c) Regarding the cases in which TMP was used, when TMP and the pH controller shown in FIG. 1 were used and the pH was controlled at 13±0.5, the best results were obtained. That is, it was found that the white powder HMBP of the formula (2) could be obtained at high yield without generating diphenoquinone by controlling the pH at 13±0.5 which was a higher pH region.

(d) Even in the cases in which TMP was used, when the pH control was not carried out, the yield was decreased, the generation of diphenoquinones was confirmed and the yellow powders were obtained.

(e) Concerning the Comparative Example 5, which was carried out using a boron compound as a pH controlling agent according to the method of JP-A-60-152433, the yield thereof was lower than that of the present invention, diphenoquinone was confirmed, and the yellow powder was obtained.

Then, the present invention 2 will be explained more in detail with reference to Examples hereinafter. A number average molecular weight and a weight average molecular weight were measured according to the gel permeation chromatography (GPC) method. Data processing was carried out according to the GPC curve and molecular weight calibration curve of a sample. The molecular weight calibration curve was obtained by making an approximation of a relation between the molecular weight of a standard polystyrene and the dissolution time thereof with the following equation, $$\mathrm{Log}M = A_0X^3 + A_1X^2 + A_2X + A_3 + A_4/X^2$$

wherein M: a molecular weight, X: an elution time −19 (minutes), and A: a coefficient. A hydroxyl group equivalent was determined from an absorption intensity at 3,600 cm$^{-1}$ in an IR analysis (liquid cell method; cell length=1 mm) using 2,6-dimethylphenol as a standard reference material.

Example 3

A longitudinally long reactor having a volume of 12 liters and equipped with a stirrer, a thermometer, an air-introducing tube and baffleplates was charged with 2.77 g (12.5 mmol) of CuBr$_2$, 0.62 g (3.6 mmol) of N,N'-di-t-butylethylenediamine, 7.43 g (73.5 mmol) of n-butyldimethylamine, 5.84 g (45.3 mmol) of di-n-butylamine and 2,600 g of toluene. The components were stirred at a reaction temperature of 40° C. A mixed solution, which was previously obtained by dissolving 129.32 g (0.48 mol) of HMBP, 175.31 g (1.44 mol) of 2,6-dimehtylphenol, 1.19 g (6.9 mmol) of N,N'-di-t-butylethylenediamine, 14.83 g (146.8 mmol) of n-butyldimethylamine and 11.71 g (90.8 mmol) of di-n-butylamine in 2,300 g of methanol (molar ratio of HMBP of the formula (2): monovalent phenol of the formula (3)=1:3, amine division ratio 1:2), was dropwise added to the reactor under stirring over 230 minutes while carrying out bubbling with a nitrogen-air mixed gas having an oxygen concentration of 8% at a flow rate of 5.2 L/min. After the completion of the addition, 1,500 g of water containing 14.26 g (37.5 mmol) of dissolved tetrasodium ethylenediamine tetraacetate was added to the reaction mixture to terminate the reaction. An aqueous layer and an organic layer were separated. The organic layer was washed with 0.6N hydrochloric acid aqueous solution and then washed with pure water. The thus-obtained solution was concentrated by an evaporator, and then drying under reduced pressure was carried out, to obtain 296.8 g of a bifunctional phenylene ether oligomer compound. The oligomer compound had a number average molecular weight of 660, a weight average molecular weight of 940 and a hydroxyl group equivalent of 330. Further, in the present reaction, samplings were carried out at 50 minutes, 100 minutes, 150 minutes and 200 minutes, and the amount of unreacted 2,6-dimethylphenol and a number average molecular weight were measured by GPC. Table 2 shows the results.

Example 4

A longitudinally long reactor having a volume of 12 liters and equipped with a stirrer, a thermometer, an air-introducing tube and baffleplates was charged with 3.88 g (17.4 mmol) of CuBr$_2$, 0.85 g (4.9 mmol) of N,N'-di-t-butylethylenediamine, 10.40 g (102.8 mmol) of n-butyldimethylamine, 8.21 g (63.5mmol) of di-n-butylamine and 2,600 g of toluene. The components were stirred at a reaction temperature of 40° C. A mixed solution, which was previously obtained by dissolving 129.32 g (0.48 mol) of HMBP, 292.63 g (2.40 mol) of 2,6-dimehtylphenol, 1.70 g (9.9 mmol) of N,N'-di-t-butylethylenediamine, 20.80 g (205.6 mmol) of n-butyldimethylamine and 16.43 g (127.1 mmol) of di-n-butylamine in 2,300 g of methanol (molar ratio of HMBP of the formula (2): monovalent phenol of the formula (3)=1:5, amine division ratio 1:2), was dropwise added to the reactor under stirring over 230 minutes while carrying out bubbling with a nitrogen-air mixed gas having an oxygen concentration of 8% at a flow rate of 5.2 L/min. After the completion of the addition, 1,500 g of water containing 19.84 g (52.2 mmol) of dissolved tetrasodium ethylenediamine tetraacetate was added to the reaction mixture to terminate the reaction. An aqueous layer and an organic layer were separated. The organic layer was washed with 0.6N hydrochloric acid aqueous solution and then washed with pure water. The thus-obtained solution was concentrated by an evaporator, and then drying under reduced pressure was carried out, to obtain 410.6 g of a bifunctional phenylene ether oligomer compound. The oligomer compound had a number average molecular weight of 920, a weight average molecular weight of 1,330 and a hydroxyl group equivalent of 465. Further, in the present reaction, samplings were carried out at 50 minutes, 100 minutes, 150 minutes and 200 minutes, and the amount of unreacted 2,6-dimethylphenol and a number average molecular weight were measured by GPC. Table 2 shows the results.

Example 5

A longitudinally long reactor having a volume of 12 liters and equipped with a stirrer, a thermometer, an air-introducing tube and baffleplates was charged with 6.64 g (29.9 mmol) of CuBr$_2$, 1.48 g (8.6 mmol) of N,N'-di-t-butylethylenediamine, 17.82 g (176.5 mmol) of n-butyldimethylamine, 14.01 g (108.6 mmol) of di-n-butylamine and 2,600 g of toluene. The components were stirred at a reaction temperature of 40° C. A mixed solution, which was previously obtained by dissolving 129.32 g (0.48 mol) of HMBP, 584.38 g (4.79 mol) of 2,6-dimehtylphenol, 2.87 g (16.7 mmol) of N,N'-di-t-butylethylenediamine, 35.59 g (352.46 mmol) of n-butyldimethylamine and 28.10 g (217.8 mmol) of di-n-butylamine in 2,300 g of methanol (molar ratio of HMBP of the formula (2): monovalent phenol of the formula (3)=1:10, amine division ratio 1:2), was dropwise added to the reactor over 230 minutes under stirring while carrying out bubbling with a nitrogen-air mixed gas having an oxygen concentration of 8% at a flow rate of 5.2 L/min. After the completion of the addition, 1,500 g of water containing 34.09 g (89.4 mmol) of dissolved tetrasodium ethylenediamine tetraacetate was added to the reaction mixture to terminate the reaction. An aqueous layer and an organic layer were separated. The organic layer was washed with 0.6N hydrochloric acid aqueous solution and then washed with pure water. The thus-obtained solution was concentrated by an evaporator, and then drying under reduced pressure was carried out, to obtain 702.2 g of a bifunctional phenylene ether oligomer compound. The oligomer compound had a number average molecular weight of 1,480, a weight average molecular weight of 2,190 and a hydroxyl group equivalent of 760. Further, in the present reaction, samplings were carried out at 50 minutes, 100 minutes, 150 minutes and 200 minutes, and the amount of unreacted 2,6-dimethylphenol and a number average molecular weight were measured by GPC. Table 2 shows the results.

Example 6

A longitudinally long reactor having a volume of 12 liters and equipped with a stirrer, a thermometer, an air-introducing tube and baffleplates was charged with 3.88 g (17.4 mmol) of CuBr$_2$, 0.85 g (4.9 mmol) of N,N'-di-t-butylethylenediamine, 10.40 g (102.8 mmol) of n-butyldimethylamine, 8.21 g (63.5 mmol) of di-n-butylamine and 2,600 g of methyl ethyl ketone. The components were stirred at a reaction temperature of 40° C. A mixed solution, which was previously obtained by dissolving 129.32 g (0.48 mol) of HMBP, 292.63 g (2.40 mol) of 2,6-dimehtylphenol, 1.70 g (9.9 mmol) of N,N'-di-t-butylethylenediamine, 20.80 g (205.6 mmol) of n-butyldimethylamine and 16.43 g (127.1 mmol) of di-n-butylamine in 2,300 g of methyl ethyl ketone (molar ratio of HMBP of the formula (2): monovalent phenol of the formula (3)=1:5, amine division ratio 1:2), was dropwise added to the reactor over 230 minutes under stirring while carrying out bubbling with a nitrogen-air mixed gas having an oxygen concentration of 8% at a flow rate of 5.2 L/min. After the completion of the addition, 1,500 g of water containing 19.84 g (52.2 mmol) of dissolved tetrasodium ethylenediamine tetraacetate was added to the reaction mixture to terminate the reaction. An aqueous layer and an organic layer were separated. The organic layer was washed with 0.6N hydrochloric acid aqueous solution and then washed with pure water. The thus-obtained solution was concentrated by an evaporator, and then drying under reduced pressure was carried out, to obtain 408.4 g of a bifunctional phenylene ether oligomer compound.

The oligomer compound had a number average molecular weight of 930, a weight average molecular weight of 1,350 and a hydroxyl group equivalent of 470. Further, in the present reaction, samplings were carried out at 50 minutes, 100 minutes, 150 minutes and 200 minutes, and the amount of unreacted 2,6-dimethylphenol and a number average molecular weight were measured by GPC. Table 2 shows the results.

Example 7

A longitudinally long reactor having a volume of 12 liters and equipped with a stirrer, a thermometer, an air-introducing tube and baffleplates was charged with 3.88 g (17.4 mmol) of $CuBr_2$, 0.85 g (4.9 mmol) of N,N'-di-t-butylethylenediamine, 10.40 g (102.8 mmol) of n-butyldimethylamine, 8.21 g (63.5 mmol) of di-n-butylamine and 2,600 g of toluene. The components were stirred at a reaction temperature of 40° C. A mixed solution, which was previously obtained by dissolving 129.32 g (0.48 mol) of HMBP, 292.63 g (2.40 mol) of 2,6-dimehtylphenol, 1.70 g (9.9 mmol) of N,N'-di-t-butylethylenediamine, 20.80 g (205.6 mmol) of n-butyldimethylamine and 16.43 g (127.1 mmol) of di-n-butylamine in 2,300 g of methanol (molar ratio of HMBP of the formula (2): monovalent phenol of the formula (3)=1:5, amine division ratio 1:2), was dropwise added to the reactor over 95 minutes under stirring while carrying out bubbling with 3.5 L/min of air. During the above dropwise addition, 3.5 L/min of a nitrogen gas was flowed into a gaseous phase. After the completion of the addition, 1,500 g of water containing 19.84 g (52.2 mmol) of dissolved tetrasodium ethylenediamine tetraacetate was added to the reaction mixture to terminate the reaction. An aqueous layer and an organic layer were separated. The organic layer was washed with 0.6N hydrochloric acid aqueous solution and then washed with pure water. The thus-obtained solution was concentrated by an evaporator, and then drying under reduced pressure was carried out, to obtain 412.6 g of a phenylene ether oligomer compound. The oligomer compound had a number average molecular weight of 910, a weight average molecular weight of 1,310 and a hydroxyl group equivalent of 460. Further, in the present reaction, samplings were carried out at 25 minutes, 50 minutes and 75 minutes, and the amount of unreacted 2,6-dimethylphenol and a number average molecular weight were measured by GPC. Table 2 shows the results.

Comparative Example 8

A longitudinally long reactor having a volume of 12 liters and equipped with a stirrer, a thermometer, an air-introducing tube and baffleplates was charged with 3.88 g (17.4 mmol) of $CuBr_2$, 2.55 g (14.8 mmol) of N,N'-di-t-butylethylenediamine, 31.20 g (308.4 mmol) of n-butyldimethylamine, 24.63 g (190.6 mmol) of di-n-butylamine and 2,600 g of toluene. The components were stirred at a reaction temperature of 40° C. A mixed solution, which was previously obtained by dissolving 129.32 g (0.48 mol) of HMBP and 292.63 g (2.40 mol) of 2,6-dimehtylphenol in 2,300 g of methanol(molar ratio of HMBP of the formula (2): monovalent phenol of the formula (3)=1:5), was dropwise added to the reactor over 230 minutes under stirring while carrying out bubbling with a nitrogen-air mixed gas having an oxygen concentration of 8% at a flow rate of 5.2 L/min. After the completion of the addition, 1,500 g of water containing 19.84 g (52.2 mmol) of dissolved tetrasodium ethylenediamine tetraacetate was added to the reaction mixture to terminate the reaction. An aqueous layer and an organic layer were separated. The organic layer was washed with 0.6N hydrochloric acid aqueous solution and then washed with pure water. The thus-obtained solution was concentrated by an evaporator, and then drying under reduced pressure was carried out, to obtain 412.1 g of a bifunctional phenylene ether oligomer compound. The oligomer compound had a number average molecular weight of 1,520, a weight average molecular weight of 3,070 and a hydroxyl group equivalent of 800. Further, in the present reaction, samplings were carriedout at 50 minutes, 100 minutes, 150 minutes and 200 minutes, and the amount of unreacted 2,6-dimethylphenol and a number average molecular weight were measured by GPC. Table 2 shows the results.

Comparative Example 9

A longitudinally long reactor having a volume of 12 liters and equipped with a stirrer, a thermometer, an air-introducing tube and baffleplates was charged with 3.88 g (17.4 mmol) of $CuBr_2$, 0.85 g (4.9 mmol) of N,N'-di-t-butylethylenediamine, 10.40 g (102.8 mmol) of n-butyldimethylamine, 8.21 g (63.5 mmol) of di-n-butylamine and 2,600 g of toluene. The components were stirred at a reaction temperature of 40° C. A mixed solution, which was previously obtained by dissolving 129.32 g (0.48 mol) of HMBP, 292.63 g (2.40 mol) of 2,6-dimethylphenol, 1.70 g (9.9 mmol) of N,N'-di-t-butylethylenediamine, 20.80 g (205.6 mmol) of n-butyldimethylamine and 16.43 g (127.1 mmol) of di-n-butylamine in 2,300 g of methanol (molar ratio of HMBP of the formula (2): monovalent phenol of the formula (3)=1:5, amine division ratio 1:2), was dropwise added to the reactor over 120 minutes under stirring while carrying out bubbling with a nitrogen-air mixed gas having an oxygen concentration of 8% at a flow rate of 5.2 L/min. When the dropwise addition was finished, 20.0% of unreacted 2,6-dimethyl phenol remained, so that stirring was continued for 100 minutes while carrying out bubbling with oxygen-containing mixed gas. Then, 1,500 g of water containing 19.84 g (52.2 mmol) of dissolved tetrasodium ethylenediamine tetraacetate was added to the reaction mixture to terminate the reaction. An aqueous layer and an organic layer were separated. The organic layer was washed with 0. 6N hydrochloric acid aqueous solution and then washed with pure water. The thus-obtained solution was concentrated by an evaporator, and then drying under reduced pressure was carried out, to obtain 407.4 g of a bifunctional phenylene ether oligomer compound. The oligomer compound had a number average molecular weight of 1,040, a weight average molecular weight of 1,940 and a hydroxyl group equivalent of 850. Since the oxidation reaction 30 was carried out in the state in which the 2,6-dimethylphenol was present in a large amount, a homopolymer of the 2,6-dimethylphenol was formed so that the hydroxyl group equivalent increased. Further, in the present reaction, samplings were carried out at 50 minutes, 100 minutes, 150 minutes and 200 minutes, and the amount of unreacted 2,6-dimethylphenol and a number average molecular weight were measured by GPC. Table 2 shows the results.

Comparative Example 10

A longitudinally long reactor having a volume of 12 liters and equipped with a stirrer, a thermometer, an air-introducing tube and baffleplates was charged with 3.88 g (17.4 mmol) of $CuBr_2$, 0.85 g (4.9 mmol) of N,N'-di-t-butylethylenediamine, 10.40 g (102.8 mmol) of n-butyldimethylamine, 8.21 g (63.5 mmol) of di-n-butylamine and 2,600 g of toluene. The components were stirred at a reaction temperature of 40° C. A mixed solution, which was previously obtained by dissolving 129.32 g (0.48 mol) of HMBP, 292.63 g (2.40 mol) of 2,6-dimehtylphenol, 1.70 g (9.9 mmol) of N,N'-di-t-butylethylenediamine, 20.80 g (205.6 mmol) of n-butyldimethylamine and 16.43 g (127.1 mmol) of di-n-butylamine in 2,300 g of methanol (molar ratio of HMBP of the formula (2): monovalent phenol of the formula (3)=1:5, amine division ratio 1:2), was dropwise added to the reactor over 95 minutes under stirring while carrying out bubbling with 3.5 L/min of air. During the above dropwise addition, 3.5 L/min of a nitrogen gas was flowed into a gaseous phase. After the completion of the addition, stirring was continued for 40 minutes while carrying out bubbling with air. 1,500 g of water containing 19.84 g (52.2 mmol) of dissolved tetrasodium ethylenediamine tetraacetate was added to the reaction mixture to terminate the reaction. An aqueous layer and an organic layer were separated. The organic layer was washed with 0.6N hydrochloric acid aqueous solution and then washed with pure water. The thus-obtained solution was concentrated by an evaporator, and then drying under reduced pressure was carried out, to obtain 414.3 g of a bifunctional phenylene ether oligomer compound. The oligomer compound had a number average molecular weight of 1,350, a weight average molecular weight of 2,510 and a hydroxyl group equivalent of 740. Further, in the present reaction, samplings were carried out at 25 minutes, 50 minutes, 75 minutes, 100 minutes and 125 minutes, and the amount of unreacted 2,6-dimethylphenol and a number average molecular weight were measured by GPC. Table 2 shows the results.

Comparative Example 11

A longitudinally long reactor having a volume of 2 liters and equipped with a stirrer, a thermometer and baffleplates was charged with 500 ml of toluene, 200 g of a commercially-available polyphenylene ether resin (supplied by Mitsubishi Gas Chemical Co., Inc., number average molecular weight: 22,000) and 24 g (105.3 mmol) of bisphenol A. The components were dissolved by stirring at 85° C. 24 g (170.7 mmol) of benzoyl peroxide was added to the resultant solution and the mixture was stirred for 60 minutes. The reaction mixture was concentrated and then dried under reduced pressure to obtain 202 g of a redistributed phenylene ether oligomer compound. The oligomer compound had a number average molecular weight of 1,280, a weight average molecular weight of 6,620 and a hydroxyl group equivalent of 890.

TABLE 2

| Bivalent/monovalent Phenol molar ratio | Example 3 1/3 | | Example 4 1/5 | | Example 5 1/10 | | Example 6 1/5 | | Example 7 1/5 | |
|---|---|---|---|---|---|---|---|---|---|---|
| | Mn | Unreacted 2,6-x | Mn | Unreacted 2,6-x | Mn | Unreacted 2,6-x | Mn | Unreacted 2,6-x | Mn | Unreacted 2,6-x |
| Reaction time | | | | | | | | | | |
| 25 minute | | | | | | | 850 | 2.0% | | |
| 50 minute | 600 | 1.5% | 880 | 1.8% | 1,310 | 3.1% | 890 | 1.8% | 910 | 1.4% |
| 75 minute | | | | | | | | | 920 | 0.9% |
| 100 minute | 630 | 1.0% | 900 | 1.2% | 1,440 | 2.1% | 930 | 1.1% | | |
| 125 minute | | | | | | | | | | |
| 150 minute | 650 | 0.8% | 920 | 1.1% | 1,460 | 1.5% | 920 | 1.0% | | |
| 200 minute | 660 | 0.5% | 910 | 1.0% | 1,470 | 0.8% | 920 | 0.9% | | |
| Finished | 660 | 0.2% | 920 | 0.4% | 1,480 | 0.5% | 930 | 0.3% | 910 | 0.2% |
| Mn | 660 | | 920 | | 1,480 | | 930 | | 910 | |
| Mw | 940 | | 1,330 | | 2,190 | | 1,350 | | 1,310 | |
| Mw/Mn | 1.42 | | 1.45 | | 1.48 | | 1.45 | | 1.44 | |
| hydroxyl group equivalent | 330 | | 465 | | 760 | | 470 | | 460 | |
| MEK solubility | ◯ | | ◯ | | ◯ | | ◯ | | ◯ | |

| | Comparative Example 8 1/5 | | Comparative Example 9 1/5 | | Comparative Example 10 1/5 | | Comparative Example 11 — |
|---|---|---|---|---|---|---|---|
| Bivalent/monovalent Phenol molar ratio | Mn | Unreacted 2,6-x | Mn | Unreacted 2,6-x | Mn | Unreacted 2,6-x | Mn |
| Reaction time | | | | | | | |
| 25 minute | | | | | 900 | 2.0% | — |
| 50 minute | 1,550 | 0.0% | 560 | 22.0% | 925 | 1.3% | — |
| 75 minute | | | | | 935 | 1.0% | |
| 100 minute | 1,530 | 0.0% | 600 | 20.0% | 940 | 1.0% | — |
| 125 minute | | | | | 1,240 | 0.2% | |
| 150 minute | 1,490 | 0.3% | 860 | 3.5% | | | — |

TABLE 2-continued

| | | | | | | | |
|---|---|---|---|---|---|---|---|
| 200 minute | 1,500 | 0.1% | 980 | 0.8% | | | — |
| Finished | 1,520 | 0.1% | 1,040 | 0.0% | 1,350 | 0.0% | 1,280 |
| Mn | | 1,520 | | 1,040 | | 1,350 | 1,280 |
| Mw | | 3,070 | | 1,940 | | 2,510 | 6,620 |
| Mw/Mn | | 2.02 | | 1.87 | | 1.86 | 5.17 |
| hydroxyl group equivalent | | 800 | | 850 | | 740 | 890 |
| MEK solubility | | Δ | | ○ | | ○ | × |

Mn: number average molecular weight, Mw: weight average molecular weight, 2,6-X: 2,6-dimethylphenol, MEK: methyl ethyl ketone From the results of the Comparative Example 8, it was found that, when amine was present in a remarkably excessive amount at the beginning of the reaction, the molecular weight increased so that it became difficult to control the molecular weight at a desired molecular weight. From the results of the Comparative Example 9, it was found that, when 15% or more of monovalent phenol was present in the reactor, a monovalent phenylene ether oligomer compound was generated due to homopolymerization of only the monovalent phenol so that it was impossible to obtain a bifunctional phenylene ether oligomer compound efficiently. From the results of the Comparative Example 10, it was found that, when stirring was continued with carrying out bubbling with air after the completion of dropwise addition of the phenol solution, an increase in molecular weight occurred so that a bifunctional phenylene ether oligomer compound having a desired molecular weight could not obtained.

Effect of the Invention

According to the production process of the present invention 1, there is provided a process for producing HMBP without generating diphenoquinone by controlling pH during a reaction at ±1 within the range of 8 to 14, preferably 11.5 to 13.5.

According to the production process of the present invention 2, there is provided a process for efficiently producing a bifunctional phenylene ether oligomer compound having a desired molecular weight. Since the bifunctional phenylene ether oligomer compound obtained according to the present invention 2 is soluble in a general-purpose solvent such as MEK, it can be easily used in broad uses. Further, its basic structure is a polyphenylene ether structure so that it is excellent in heat resistance and dielectric characteristic and can be applied to electric and electronic materials.

What is claimed is:

1. A process for producing a bifunctional phenylene ether oligomer compound having a controlled average molecular weight, represented by the formula (5), comprising carrying out oxidation polymerization at an oxygen concentration lower than an oxygen concentration of an explosion limit of a solvent to be used by charging a reactor with a mixture containing a catalyst, an amine and a solvent in advance and then dropwise adding a mixture containing 2,2',3,3',5,5'-hexamethyl-(1,1'-biphenyl)-4,4'-diol of the following formula (2), a monovalent phenol of the following formula (6), an amine and a solvent to the mixture in the reactor, thereby producing a bifunctional phenylene ether oligomer of the formula (5), wherein, from a moment when the number average molecular weight of the bifunctional phenylene ether oligomer compound exceeds 500, the supply rate of the dropwise addition mixture is controlled such that the concentration of the monovalent phenol of the formula (6) in the reactor does not exceed 15% by weight based on the total amount of the above monovalent phenol, the bifunctional phenylene ether oligomer and the 2,2',3,3',5,5'-hexamethyl-(1,1'-biphenyl)-4,4'-diol [(6)/(5)+(2)+(6)<0.15], in which $R^1$ and $R^2$ may be the same or different and are a halogen atom, an alkyl group having 6 or less carbon atoms or a phenyl group, $R^3$ and $R^4$ may be the same or different and are a hydrogen atom, a halogen atom, an alkyl group having 6 or less carbon atoms or a phenyl group, and each of m and n is an integer of 0 to 25 while at least one of m and n is not 0.

2. A process according to claim 1, wherein the mixture containing the catalyst, the amine and the solvent charged in the reactor in advance further contains 2,2',3,3',5,5'-hexamethyl-(1,1'-biphenyl)-4,4'-diol.

3. A process according to claim 1, wherein the amount of the amine in the mixture charged in the reactor in advance is 20 to 70% by weight based on a required amine amount and the residual amine in an amount of 30 to 80% by weight is contained in the dropwise addition mixture.

4. A process according to claim 1,
wherein the oxygen concentration in the reactor is 3 to 15% by volume.

5. A process according to claim 1,
wherein the monovalent phenol of the formula (6) is 2,6-dimethylphenol alone or a mixture of 2,6-dimethylphenol and 2,3,6-trimethylphenol.

6. A process according to claim 1,
wherein the molar ratio between the 2,2',3,3',5,5'-hexamethyl-(1,1'-biphenyl)-4,4'-diol of the formula (2) and the monovalent phenol of the formula (6) is 1:1 to 1:15.

* * * * *